US00PP09823P

United States Patent [19]

Rabb

[11] Patent Number: Plant 9,823

[45] Date of Patent: Mar. 11, 1997

[54] CHRYSANTHEMUM PLANT NAMED 'CORAL SPLENDOR'

[76] Inventor: Frederick H. Rabb, Box 21, Site 14, RR 1, Strathmore, Alta, Canada, T1P 1J6

[21] Appl. No.: 514,553

[22] Filed: Aug. 14, 1995

[51] Int. Cl.[6] ..... A01H 5/00

[52] U.S. Cl. ..... Plt./74.1

[58] Field of Search ..... Plt./74.1, 82.3, Plt./82.4

[56] References Cited

U.S. PATENT DOCUMENTS

P.P. 5,225 5/1984 Duffett ..... Plt./82.4
4,616,099 10/1986 Sparkes ..... 47/58

OTHER PUBLICATIONS

Broertjes, et al., 1980, "A mutant of a mutant of a . . . Irradiation of progressive radiation–induced mutants in a mutation breeding programme with *Chrysanthemum morifolium*", Euphytica, 29:525–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X–rays", Am. Soc. Hort. Sci. Proc., pp. 613–620.

Broertjes, 1966, "Mutation breeding of Chrysanthemums", Euphytica, 15:156–162.

Dowrick, et al., 1966, "The induction of mutations in chrysanthemum using X– and gamma radiation", Euphytica, 15:204–210.

*Primary Examiner*—Howard J. Locker
*Attorney, Agent, or Firm*—Foley & Lardner

[57] ABSTRACT

A Chrysanthemum plant named Coral Splendor particularly characterized by its flat capitulum form; daisy capitulum type; coral ray floret color; diameter across face of capitulum of 145 to 160 mm when fully opened, when grown as a pinched disbudded pot mum; photoperiodic flowering response to short days of 54 to 60 days; plant height, with 14 long days after sticking unrooted cuttings and with 1 to 2 applications of 2500 ppm B-9 SP, ranges from 29 to 30 cm when grown as a pinched pot mum with 4 cuttings in a 15 cm pot; upright branching pattern; and recommended as a disbudded pot mum.

1 Drawing Sheet

The present invention comprises a new and distinct cultivar of Chrysanthemum, botanically known as *Dendranthema grandiflora,* and referred to by the cultivar name Coral Splendor.

Coral Splendor, identified as 6921 (91-02060), is a spontaneous mutation of the cultivar Splendor, disclosed in U.S. Plant Pat. No. 5,225, and was selected to expand the color range of the parental variety.

Coral Splendor was discovered and selected by inventor Frederick H. Rabb as one flowering plant within a flowering block of Splendor in June 1991, in a controlled environment in Strathmore, Alta, Canada.

The first act of asexual reproduction of Coral Splendor was accomplished when vegative cuttings were taken from the initial selection in August 1991 in a controlled environment in Strathmore, Alta, Canada by Frederick H. Rabb.

Horticultural examination of controlled flowerings of successive plantings has shown that the unique combination of characteristics as herein disclosed for Coral Splendor are firmly fixed and are retained through successive generations of asexual reproduction.

Coral Splendor has not been observed under all possible environmental conditions. The phenotype may vary significantly with variations in environment such as temperature, light intensity and daylength, without, however, any variance in genotype.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Coral Splendor, which, in combination, distinguish this Chrysanthemum as a new and distinct cultivar:

1. Flat capitulum form.
2. Daisy capitulum type.
3. Coral ray floret color.
4. Diameter across face of capitulum of 145 to 160 mm when fully opened, when grown as a pinched disbudded pot mum.
5. Photoperiodic flowering response to short days of 54 to 60 days.
6. Plant height, with 14 long days after sticking unrooted cuttings and with 1 to 2 applications of 2500 ppm B-9 SP, ranges from 23 to 30 cm when grown as a pinched pot mum with 4 cuttings in a 15 cm pot.
7. Upright branching pattern.
8. Recommended as a disbudded pot mum.

The accompanying photographic drawing is a side view of a potted mum of Coral Splendor, with 4 cuttings in a 15 cm pot, with the colors being as nearly true as possible with illustrations of this type.

Of the commercial cultivars known to the inventor, the most similar in comparison to Coral Splendor is the parent cultivar Splendor. All traits of Coral Splendor are similar to those of Splendor, except for ray floret color. The ray floret color of Coral Splendor is coral (orange to red), while the ray floret color of Splendor is described as light lavender.

In the following description color references are made to The Royal Horticultural Society Colour Chart. The color values were determined on plant material grown as a pinched disbudded pot mum in Salinas, Calif. on Aug. 23, 1994.

Classification

*Botanical.*—Dendranthema grandiflora cv Coral Splendor.

*Commercial.*—Flat daisy disbud pot mum.

INFLORESCENCE

A. Capitulum:
*Form.*—Flat
*Type.*—Daisy
*Diameter across face.*—145 to 160 mm when fully opened.

B. Corolla of ray florets: Color designations or values are for flowers which have just full opened.
*Color (general tonality from a distance of three meters).*—Coral.
*Color (upper surface).*—36A to 29C-D.
*Color (under surface).*—29D.
*Shape.*—Flat, oblong.

C. Corolla of disc florets:
*Color (mature).*—6A to 6B.
*Color (immature).*—Closest to 144C.

D. Reproductive organs:
*Androecium.*—Present on disc florets only; scant pollen.

*Gynoecium.*—Present on both ray and disc florets.

PLANT

A. General appearance:
*Height.*—23 to 30 cm when grown as a pinched pot mum with 14 long days after sticking unrooted cuttings prior to start of short days, with 1 to 2 applications of 2500 ppm B-9 SP.
*Branching pattern.*—Upright.

B. Foliage:
*Color (upper surface).*—147A.
*Color (under surface).*—147B.
*Shape.*—Moderately lobed, slightly serrated.

What is claimed is:

1. A new and distinct Chrysanthemum plant named Coral Splendor as described and illustrated.

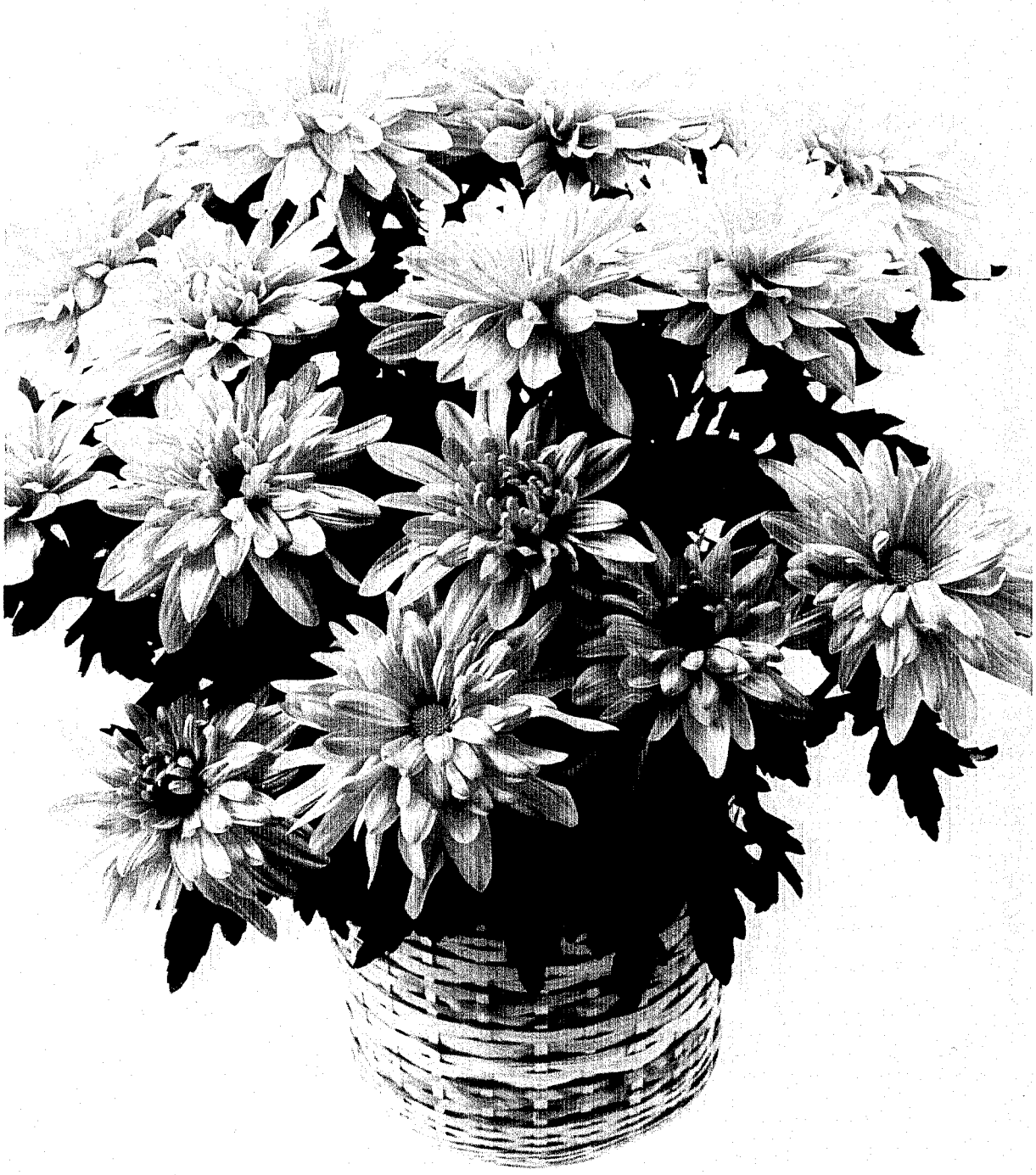

* * * * *